(12) United States Patent
Dimpfel (10) Patent No.: US 12,059,404 B2
(45) Date of Patent: Aug. 13, 2024

(54) MESEMBRENOL AND/OR MESEMBRANOL FOR PROPHYLAXIS AND TREATMENT OF PATIENTS SUFFERING FROM EPILEPSY AND ASSOCIATED DISEASES

(71) Applicant: HG&H Pharmaceuticals (Pty) Ltd, Johannesburg (ZA)

(72) Inventor: Wilfried Dimpfel, Wetzlar (DE)

(73) Assignee: HG&H Pharmaceuticals (Pty) Ltd, Johannesburg (ZA)

( * ) Notice: Subject to any disclaimer, the term of this patent is extended or adjusted under 35 U.S.C. 154(b) by 85 days.

(21) Appl. No.: 16/633,296

(22) PCT Filed: Jul. 25, 2018

(86) PCT No.: PCT/IB2018/055535
§ 371 (c)(1),
(2) Date: Jan. 23, 2020

(87) PCT Pub. No.: WO2019/021196
PCT Pub. Date: Jan. 31, 2019

(65) Prior Publication Data
US 2020/0215033 A1   Jul. 9, 2020

(30) Foreign Application Priority Data

Jul. 26, 2017 (ZA) .................. 2017/05072

(51) Int. Cl.
| A61K 31/403 | (2006.01) |
| A61K 36/185 | (2006.01) |
| A61P 25/08  | (2006.01) |

(52) U.S. Cl.
CPC .......... *A61K 31/403* (2013.01); *A61K 36/185* (2013.01); *A61P 25/08* (2018.01)

(58) Field of Classification Search
CPC .................................................... A61P 25/08
See application file for complete search history.

(56) References Cited

U.S. PATENT DOCUMENTS

| 6,271,001 B1 | 8/2001 | Clarke et al. |
| 6,288,104 B1 | 9/2001 | Gericke et al. |
| 8,552,051 B2 | 10/2013 | Harvey et al. |
| 8,980,338 B2 | 3/2015 | Gericke et al. |
| 9,381,220 B2 | 7/2016 | Gericke et al. |
| 2002/0106731 A1 | 8/2002 | Ruben et al. |
| 2004/0185429 A1 | 9/2004 | Kelleher-Andersson et al. |
| 2004/0229291 A1 | 11/2004 | Zhou et al. |
| 2004/0254152 A1 | 12/2004 | Monje et al. |
| 2005/0004046 A1 | 1/2005 | Praag et al. |
| 2005/0009742 A1 | 1/2005 | Bertilsson et al. |
| 2005/0009847 A1 | 1/2005 | Bertilsson et al. |
| 2005/0031538 A1 | 2/2005 | Steindler et al. |
| 2005/0032702 A1 | 2/2005 | Eriksson |
| 2012/0041045 A1 | 2/2012 | Harvey et al. |
| 2017/0137436 A1 | 5/2017 | Kurokawa et al. |

FOREIGN PATENT DOCUMENTS

| DE | 3604112 | 8/1987 |
| JP | 2000511896 A | 9/2000 |
| JP | 2009542815 A | 12/2009 |
| WO | 199746234 | 12/1997 |
| WO | 02092112 | 11/2002 |
| WO | 2006025920 | 3/2006 |
| WO | 2008006050 A2 | 1/2008 |
| WO | 2010106494 | 9/2010 |
| WO | 2010106495 | 9/2010 |
| WO | 2017082288 A1 | 5/2017 |

OTHER PUBLICATIONS

A toxicological safety assessment of a standardized extract of Sceletium tortuosum (Zembrin®) in rats, Food and Chemical Toxicology 74 (2014) 190-199. (Year: 2014).*
WordNet Search—3.1, Definition of Prevent, Princeton University, Available Online at: http://wordnet.princeton.edu, Accessed from Internet on Sep. 18, 2012, 1 page.
U.S. Appl. No. 13/256,674, Advisory Action mailed on Sep. 30, 2013, 3 pages.
U.S. Appl. No. 13/256,674, Final Office Action mailed on Oct. 1, 2014, 9 pages.
U.S. Appl. No. 13/256,674, Non-Final Office Action mailed on Nov. 6, 2012, 10 pages.
U.S. Appl. No. 13/256,674, Non-Final Office Action mailed on Apr. 4, 2014, 5 pages.
U.S. Appl. No. 13/256,674, Notice of Allowance mailed on Dec. 24, 2014, 9 pages.
U.S. Appl. No. 13/256,674, Pre-Brief Conference Request mailed on Oct. 21, 2013, 11 pages.
U.S. Appl. No. 13/256,674, Restriction Requirement mailed on Jun. 13, 2012, 9 pages.
U.S. Appl. No. 13/256,686, Non-Final Office Action mailed on Oct. 23, 2012, 18 pages.
U.S. Appl. No. 13/256,686, Notice of Allowance mailed on Jun. 6, 2013, 13 pages.
U.S. Appl. No. 13/272,200, Final Office Action mailed on Jul. 19, 2013, 12 pages.
U.S. Appl. No. 14/331,962, Non-Final Office Action mailed on Sep. 30, 2015, 14 pages.
U.S. Appl. No. 14/331,962, Notice of Allowance mailed on Mar. 3, 2016, 10 pages.

(Continued)

*Primary Examiner* — Aaron J Kosar
*Assistant Examiner* — Jacob A Boeckelman
(74) *Attorney, Agent, or Firm* — Kilpatrick Townsend & Stockton LLP (57) ABSTRACT

The invention relates to the alkaloids mesembranol or mesembrenol, or pharmaceutical acceptable salts or complexes thereof, for use in the prophylaxis or treatment of a disease that responds to treatment with an AMPA (α-amino-3-hydroxy-5-methyl-4-isoxazolepropionic acid) receptor antagonist. The prophylaxis or treatment attenuates AMPA mediated neurotransmission in the hippocampus of a subject.

11 Claims, 7 Drawing Sheets

(56) References Cited

OTHER PUBLICATIONS

U.S. Appl. No. 14/331,962, Restriction Requirement mailed on Feb. 6, 2015, 8 pages.
Gericke et al., Sceletium—A Review Update, Journal of Ethnopharmacology, vol. 119, No. 3, Oct. 28, 2008, pp. 653-663.
Harvey et al., Pharmacological Actions of the South African Medicinal and Functional Food Plant Sceletium Tortuosum and its Principal Alkaloids, Journal of Ethnopharmacology, vol. 137, No. 3, Oct. 11, 2011, pp. 1124-1129.
Lang et al., Asthma, Disease Management Project, Cleveland Clinic Center for Continuing Education, Available Online at: http://www.clevelandclinicmeded.com/medicalpubs/diseasemanagementlallergy/bronchial-asthma/, Accessed from Internet on: Oct. 10, 2012, 32 pages.
Napoletano et al., Mesembrine is an Inhibitor of PDE4 That Follows the Structure-Activity Relationship of Rolipram, Chemistry Preprint Archive, vol. 2001, Issue 3, Mar. 2001, 6 pages.
Patnala et al., A Capillary Zone Electrophoresis Method for the Assay and Quality Control of Mesembrine in Sceletium Tablets, Journal of Pharmaceutical and Biomedical Analysis, vol. 48, No. 2, Sep. 29, 2008, pp. 440-446.
Patnala et al., Investigations of the Phytochemical Content of Sceletium Tortuosum Following the Preparation of "Kougoed" Fermentation of Plant Material, Journal of Ethnopharmacology, vol. 121, No. 1, Jan. 12, 2009, pp. 86-91.
International Application No. PCT/IB2010/051132, International Search Report mailed on Jun. 2, 2010, 4 pages.
International Application No. PCT/IB2010/051132, Written Opinion mailed on Jun. 2, 2010, 7 pages.
International Application No. PCT/IB2010/051133, International Preliminary Report on Patentability mailed on Jun. 27, 2011, 8 pages.
International Application No. PCT/IB2010/051133, International Search Report mailed on Sep. 2, 2010, 5 pages.
International Application No. PCT/IB2010/051133, Written Opinion mailed on Sep. 2, 2010, 6 pages.
International Patent Application No. PCT/IB2018/055535, International Search Report mailed on Nov. 16, 2018, 4 pages.
International Patent Application No. PCT/IB2018/055535, Written Opinion mailed on Nov. 16, 2018, 7 pages.
Saldou et al., Comparison of Recombinant Human PDE4 Isoforms: Interaction with Substrate and Inhibitors, Cell Signal, vol. 10, No. 6, Jun. 1998, pp. 427-440.
Schmeda-Hirschmann et al., Activity of Amaryllidaceae Alkaloids on the Blood Pressure of Normotensive Rates, Pharmacy and Pharmacology Communications, vol. 6, No. 7, 2000, pp. 309-312.
Smith et al., Psychoactive Constituents of the Genus Sceletium N.E. Sr. and other Mesembryanthemaceae: A Review, Journal of Ethnopharmacology, vol. 50, No. 3, Mar. 1996, pp. 119-130.
Smith et al., The Distribution of Mesembrine Alkaloids in Selected Taxa of the Mesembryanthemaceae and Their Modification in the Sceletium Derived 'kougoed', Pharmaceutical Biology, vol. 36, No. 3, 1998, pp. 173-179.
Tatsumi et al., Pharmacological Profile of Neuroleptics at Human Monoamine Transporters, European Journal of Pharmacology, vol. 368, No. 2-3, Mar. 5, 1999, pp. 277-283.
Van Wyk, A Broad View of Commercially Important Southern African Medicinal Plants, Journal of Ethnopharmacology, vol. 119, No. 3, Oct. 2008, pp. 342-355.
Weniger et al., Cytotoxic Activity of Amaryllidaceae Alkaloids, Planta Medica, vol. 61, No. 1, 1995, pp. 77-79.
Zhang et al., Phosphodiesterase-4 as a Potential Drug Target, Expert Opinion on Therapeutic Targets, vol. 9, No. 6, Dec. 2005, pp. 1283-1305.
Gericke: "Clinical application of selected South African medicinal plants", Australian Journal of Medical Herbalism, vol. 13, No. 1, 2001, XP055521548, pp. 3-18.
Chiu et al: "Proof-of-Concept Randomized Controlled Study of Cognition Effects of the Proprietary Extract Sceletium tortuosum (Zembrin) Targeting Phosphodiesterase-4 in Cognitively Healthy Subjects: Implications for Alzheimer's Dementia", Evidence-Based Complementary and Alternative Medicine, vol. 2014, XP055521541, pp. 1-9.
Chiu et al: "Exploring Standardized Zembrin Extracts from the South African plant Sceletium tortuosum in Dual Targeting Phosphodiesterase-4 (PDE-4) and Serotonin Reuptake Inhibition as potential treatment in Schizophrenia", Internationa Journal of Complementary & Alternative Medicine, vol. 6, No. 5, May 2017 (May 2017), XP055521537, pp. 1-7.
Dimpfel: "Reverse pharmacology of Sceletium tortuosum", Clinical Pharmacology & Biopharmaceutics, vol. 06, No. 04(Suppl), Nov. 2017 (Nov. 2017), XP055521332, pp. 11-12.
Dimpfel et al: "Effect of Zembrin and four of its alkaloid constituents on electric excitability of the rat hippocampus", Journal of Ethnopharmacology, vol. 223, May 22, 2018 (May 22, 2018), XP055521521, pp. 135-141.
Japan Patent Application No. 2020-503939, Office Action (Notice of Reasons for Rejection), dated Mar. 29, 2022.
Europe Patent Application No. 18758969.2, Office Action (Communication pursuant to Article 94(3) EPC), dated May 3, 2022.
Steinhoff, *The AMPA receptor antagonist perampanel in the adjunctive treatment of partialonset seizures: clinical trial evidence and experience*, Therapeutic Advances in Neurological Disorders, 2015, vol. 8(3), pp. 137-147.
Ghosh et al., *Pharmacological and Therapeutic Approaches in the Treatment of Epilepsy*, Biomedicines, 2021, 9(470), pp. 1-14.
Perucca, *The pharmacological treatment of epilepsy: recent advances and future perspectives*, Acta Epileptologica, 2021, 3(22), pp. 1-11.
Rogawski, *Revisiting AMPA Receptors as an Antiepileptic Drug Target*, 2011, Epilepsy Currents, 11(2), pp. 56-63.
Rong et al., *SAD-B modulates epileptic seizure by regulating AMPA receptors in patients with temporal lobe epilepsy and in the PTZ-induced epileptic model*, 2019, Brazilian Journal of Medical and Biological Research, 53(4), pp. 1-10.
Steinhoff, *The AMPA receptor antagonist perampanel in the adjunctive treatment of partialonset seizures: clinical trial evidence and experience*, Therapeutic Advances in Neurological Disorders, 2015, 8(3), pp. 137-147.
Dalic et al., *Managing drug-resistant epilepsy: challenges and solutions*, Neuropsychiatric Disease and Treatment, 2016, 12, pp. 2605-2616.
Tang et al., *Drug-Resistant epilepsy: Multiple Hypotheses, Few Answers*, Frontiers in Neurology, 2017, 8(301), pp. 1-19.
Augustin et al., *Mechanisms of action for the medium-chain triglyceride ketogenic diet in neurological and metabolic disorders*, Lancet Neurology, 2018, 17, pp. 84-93.
Chang et al., *Seizure control by decanoic acid through direct AMPA receptor inhibition*, Brain, 2016, 139; pp. 431-443.
Rektor, *Perampanel, a novel, non-competitive, selective AMPA receptor antagonist as adjunctive therapy for treatment-resistant partial-onset seizures*, Expert Opinion on Pharmacotherapy, 2012, 14(2), pp. 225-235.
Lattanzi et al., *The impact of perampanel and targeting AMPA transmission on anti-seizure drug discovery*, Expert Opinion on Drug Discovery, 2019, 14(3), pp. 195-197.
Leo et al., *The role of AMPA receptors and their antagonists in status epilepticus*, Epilepsia, 2018, 59, pp. 1098-1108.
Kanner et al., *Practice guideline update summary: Efficacy and tolerability of the new antiepileptic drugs I: Treatment of new-onset epilepsy*, Neurology, 2018, 91(2), pp. 260-268.

\* cited by examiner

MESEMBRENOL AND/OR MESEMBRANOL FOR PROPHYLAXIS AND TREATMENT OF PATIENTS SUFFERING FROM EPILEPSY AND ASSOCIATED DISEASES

CROSS-REFERENCE TO RELATED APPLICATION

The present application is a U.S. national phase under 35 U.S.C. § 372 of International Patent Application No. PCT/IB2018/055535, filed Jul. 25, 2018, which claims priority to South African Patent Application No. 2017/05072, filed Jul. 26, 2017, the contents of both of which are incorporated herein by reference.

FIELD OF THE INVENTION

This invention relates to the treatment and prophylaxis of diseases that respond to treatment with an AMPA (α-amino-3-hydroxy-5-methyl-4-isoxazolepropionic acid) receptor antagonist. It relates, in particular, to the use of the alkaloids mesembranol and/or mesembrenol, or pharmaceutical acceptable salts or complexes thereof, for the treatment or prophylaxis of epilepsy.

BACKGROUND OF THE INVENTION

*Sceletium tortuosum*, a plant of the family Mesembryanthemaceae, is known to contain alkaloids such as mesembranol, mesembrenol, mesembrine and mesembrenone. In recent years *Sceletium tortuosum* has received considerable commercial interest in applications for relieving stress in healthy people, and for treating a broad range of psychological, psychiatric and inflammatory conditions (Gericke, N. (2001) Clinical application of selected South African medicinal plants. *Australas. J. Med. Herbal*, 13, 3-17). *Sceletium tortuosum* has been used as a simple masticatory, for the relief of thirst and hunger, to combat fatigue, as medicines, and for social and spiritual purposes by San hunter-gatherers (historically referred to as Bushmen) and Khoi pastoralists (historically referred to as Hottentots) for millennia before the earliest written reports of the uses of these plants by European explorers and settlers (Gericke, N., Viljoen, A. M. (2008) *Sceletium*—A review update. *Journal of Ethnopharmacology*, 119, 653-63).

Chemistry and hitherto known effects of sceletium alkaloids have been described extensively by Harvey et al. 2011 (Harvey A H, Young L C, Viljoen A M, Gericke, N P: Pharmacological action of the South African medicinal and functional food plant *Sceletium tortuosum* and its principal alkaloids (*Journal of Ethnopharmacology* (2011), 137, 1124-1129).

The applicant has surprisingly found that the aforementioned alkaloid(s) have an effect on the glutamatergic transmission in the hippocampus. In particular, it was found that mesembranol and mesembrenol most strongly affect attenuation of AMPA (α-amino-3-hydroxy-5-methyl-4-isoxazolepropionic acid) mediated neurotransmission. Attenuation of AMPA mediated neurotransmission has been shown as the mechanism of action of certain antiepileptic drugs (Steinhoff, B. J. (2015). The applicant, therefore, believes that compositions according to the invention find substantial utility in the treatment or prophylaxis of epilepsy, and associated diseases.

SUMMARY OF THE INVENTION

According to a first aspect of the invention, there is provided a composition which includes at least one of the alkaloids mesembranol and mesembrenol, or pharmaceutical acceptable salt(s) or complex(es) thereof, for use in the prophylaxis or treatment of a disease that responds to treatment with an AMPA (α-amino-3-hydroxy-5-methyl-4-isoxazolepropionic acid) receptor antagonist wherein said prophylaxis or treatment attenuates AMPA mediated neurotransmission in the hippocampus of a subject.

In accordance with the invention, the attenuation of AMPA mediated neurotransmission is effected by inducing a suppression of pyramidal cell activity upon administration of the composition.

Preferably, the composition may be for the treatment or prophylaxis of epilepsy, conditions associated with epilepsy, or seizures associated with epilepsy. Conditions and/or seizures associated with epilepsy may include migraine, cerebrovascular and cardiovascular disorders, gastrointestinal disorders, pulmonary disorders, dementia, chronic fatigue, depression, mood disorders, anxiety, personality disorders, psychotic disorders, non-epileptic seizures, cognitive dysfunction, antiepileptic drug (AED)-related neurobehavioral disorders, suicidality, and behavioral/psychiatric disturbance.

In a preferred embodiment of the invention, the composition includes mesembranol and mesembrenol.

The general formulas of these alkaloids are shown below:

mesembranol mesembrenol

The source of the alkaloids may be a plant of the family Mesembryanthemaceae, such as a plant of the species *Sceletium tortuosum*, or an extract of *Sceletium tortuosum*.

A total alkaloid content of the extract in a particular dosage may vary between 0.1% and 2% (by weight), preferably between 0.2% and 0.6% (by weight), and more preferably, 0.2% and 0.5% (by weight), and most preferably, between 0.35% and 0.45% by weight.

Preferably, the extract includes at least 5% (w/w) of mesembranol, at least 20% (w/w) of mesembrenol, or a combined content of mesembranol and mesembrenol of greater than 40% (w/w), preferably greater than 50% of total alkaloid content.

In one embodiment of the invention, the composition according to the invention comprises an extract of *Sceletium tortuosum* sold as Zembrin®, which contains a total alkaloid content of between 0.35% and 0.45% (by weight), with mesembranol comprising at least 5% (w/w) of the total alkaloid content, and mesembrenol comprising over 40% (w/w) of the total alkaloid content.

According to the invention, the alkaloids may be used in the form of their pharmaceutically acceptable salts or complexes. The preparation of such salts may be carried out according to a method known in the art. Suitable salt formers may include all customary pharmaceutically acceptable acids or anions. Coupling to glucuronic acid may also be used.

The composition may be in the form of a dietary supplement or a pharmaceutical composition.

The composition may be administered by any conventional route. In particular, the composition may be for oral administration to a subject in need thereof. However, administration by other means may also be possible, e.g. paroral, topical, parenteral, intravenous, intramuscular, subcutaneous, nasal, inhaled, rectal or transdermal.

The composition according to the invention may be for administration in the form of tablets, capsules, pills, granules, suppositories, pellets, solutions, dispersions, where the alkaloid(s) (i.e. the active ingredient(s)) may, optionally, be combined with pharmaceutically acceptable excipients and carrier substances.

The composition according to the invention may be in a solution form, wherein the solution preferably comprises 0.5 to 2% by weight, particularly preferably 0.6 to 1% by total weight of the active ingredient(s).

The composition according to the invention may be in a solid form, wherein the active ingredient(s) are combined with an active ingredient extender, including lactose, dextrose, sucrose, cellulose, maize starch or potato starch; lubricants, e.g. silicate, talc, stearic acid, magnesium or calcium stearate and/or polyethylene glycols; binding agents, e.g. starches, gum arabic, gelatin, methylcellulose, carboxymethylcellulose or polyvinylpyrrolidone: pulping agents, e.g. starch, alginic acid, alginates or sodium starch glycolates, foaming mixtures; coloring agents; sweeteners; wetting agents such as lecithin, polysorbates, lauryl sulfates; generally non-toxic and pharmacologically inactive excipient used in pharmaceutical formulations.

The composition may be manufactured or formulated according to a method known in the art, e.g. by mixing, granulating, pelletizing, sugar coating or overlay coating process.

The composition according to the invention may be a liquid dispersion for oral administration and may include a syrup, emulsion or suspension. The syrup may include a carrier, e.g. sucrose or sucrose with glycerin and/or mannitol and/or sorbitol.

The composition according to the invention may be a suspension and/or an emulsion and may include a carrier, e.g. a natural resin, agar, sodium alginate, pectin, methylcellulose, carboxymethylcellulose or polyvinyl alcohol.

The composition according to the invention may be a suspension or solution for intramuscular administration by means of injection, wherein the suspension or solution comprises the active ingredient(s), and optionally a pharmaceutically acceptable carrier, e.g. sterile water, olive oil, ethyl oleate, glycols, e.g. propylene glycol, and further optionally, a suitable amount of lidocaine hydrochloride.

The composition according to the invention may be a solution for intravenous injection or infusion and may include a carrier, e.g. sterile water or, preferably, a sterile, aqueous, isotonic salt solution.

The composition in accordance with the invention may include a pharmaceutical carrier. The carrier may include cocoa butter, polyethylene glycol, a polyoxyethylene sorbitol fatty acid ester and lecithin.

The composition in accordance with the invention may be for topical application. In particular, the composition may be in the form of a cream, a lotion or a paste. Even more particularly, the composition may be prepared by mixing the active ingredient(s) with a conventional oily or emulsifying carrier.

In accordance with the invention, the dosage unit and dosage rate of the composition may be as follows:

A Composition for Oral Administration:

A daily dose of 0.2 to 2 mg of active ingredient(s), preferably 1 to 1.5 mg active ingredient(s). The daily dose can, for example, be administered in 1 to 3 single doses, preferably in two single doses.

A Composition for Parenteral Administration (for Example Intravenous, Subcutaneous, Intramuscular):

A daily dose of 0.1 to 1 mg of active ingredient(s), preferably 0.5 mg of active ingredient(s). The daily dose can, for example, be administered in 1 to 3 single doses, preferably in a single dose.

A Composition for Rectal Administration:

A daily dose of 0.5 to 4 mg of active ingredient(s), preferably 1.5 mg of active ingredient(s) per day dose. The daily dose can, for example, be administered daily in 1 to 3 single doses, preferably in a single dose.

As a Dietary Supplement Such as Zembrin®:

A daily dose of from 10 to 200 mg of Zembrin extract, preferably 25-70 mg.

It will be appreciated that, in the case where a pharmaceutically acceptable salt is used, a specialist in an existing known method must appropriately adapt the dosage.

The invention also extends to a method of modulating and/or inhibiting AMPA ($\alpha$-amino-3-hydroxy-5-methyl-4-isoxazolepropionic acid) receptor activity comprising administering to an individual at least one of the alkaloids, mesembranol or mesembrenol, or pharmaceutical acceptable salts or complexes thereof.

Preferably, the method may be for the treatment or prophylaxis of epilepsy, a condition associated with epilepsy, or seizures associated with epilepsy.

In a preferred embodiment of the invention, the method includes administering mesembranol and mesembrenol, or pharmaceutical acceptable salts or complexes thereof.

The invention also extends to the use of at least one of the alkaloids mesembranol or mesembrenol, or pharmaceutical acceptable salts or complexes thereof, in the manufacture of a composition for the prophylaxis or treatment of diseases that respond to treatment with an AMPA ($\alpha$-amino-3-hydroxy-5-methyl-4-isoxazolepropionic acid) receptor antagonist wherein said composition attenuates AMPA mediated neurotransmission in the hippocampus of a subject.

In accordance with the invention, the attenuation of AMPA mediated neurotransmission is effected by inducing a suppression of pyramidal cell activity upon administration of the composition.

Preferably, the composition may be for the treatment or prophylaxis of epilepsy, conditions associated with epilepsy, or seizures associated with epilepsy. Conditions and/or seizures associated with epilepsy may include migraine, cerebrovascular and cardiovascular disorders, gastrointestinal disorders, pulmonary disorders, dementia, chronic fatigue, depression, mood disorders, anxiety, personality disorders, psychotic disorders, non-epileptic seizures, cognitive dysfunction, antiepileptic drug (AED)-related neurobehavioral disorders, suicidality, and behavioral/psychiatric disturbance.

DETAILED DESCRIPTION OF THE INVENTION

The invention is now described according to the following non-limiting examples and with reference to the accompanying diagrammatic drawings, in which the figures represent the following.

EXAMPLE A

Method of Testing Long Term Potentiation in the Hippocampus

Electric stimulation of Schaffer Collaterals leads to release of glutamate resulting in excitation of the postsynaptic pyramidal cells. The result of the electric stimulation can be recorded as so-called population spike (pop-spike). The amplitude of the resulting population spike represents the number of recruited pyramidal cells. The model of hippocampal pyramidal cell activity reflects the effects of physiological interventions by an increase or decrease of the amplitude of the population spike.

This model can also be used under ex vivo conditions. In this case, the preparation is administered daily for a week and the hippocampus is taken out the next day for in vitro characterization of the sensitivity of the intra-hippocampal pathway to electric stimulation. Within a second step, the mechanism of action of the preparation under investigation can be approached by testing its action in the presence of several receptor agonists of glutamatergic transmission. If such a selective compound fails to exert its usual action, a clue to the mechanism of action of the preparation under investigation is given with respect to ionotrophic or metabotrophic glutamate receptors.

Hippocampus slices were obtained from 19 adult male Sprague-Dawley rats (Charles River Wiga, Sulzbach, Germany). Rats were kept under a reversed day/night cycle for 2 weeks prior to the start of the experiments to allow recording of in vitro activity from slices during the active phase of their circadian rhythm (Dimpfel, W., Dalhoff, B., Hofmann, W., Schlüter, G. (1994) Electrically evoked potentials in the rat hippocampus slice in the presence of aminophylline alone and in combination with quinolones (*European Neuropsychopharmacology*, 4, 151-156).

Preparation of the slices was performed exactly as reported earlier (Dimpfel, W. and Hoffmann, J. A. (2011) Effects of rasagiline, its metabolite aminoindan and selegiline on glutamate receptor mediated signalling in the rat hippocampus slice in vitro (*BMC Pharmacology*, 11, 2)). Animals were exsanguinated under ether anaesthesia; the brain was removed in total and the hippocampal formation was isolated under microstereoscopic sight. The midsection of the hippocampus was fixed to the table of a vibrating microtome (Rhema Labortechnik, Hofheim, Germany) using a cyanoacrylate adhesive, submerged in chilled bicarbonate-buffered saline (artificial cerebrospinal fluid (ACSF): NaCl: 124 mM, KCl: 5 mM, $CaCl_2$: 2 mM, $MgSO_4$: 2 mM, $NaHCO_3$: 26 mM, glucose: 10 mM, and cut into slices of 400µ thickness. All slices were pre-incubated for at least 1 h in Carbogen saturated ACSF (pH 7.4) in a pre-chamber before use (Dimpfel, W., Spüler, M., Dalhoff, A., Hoffmann, W., Schlüter, G. (1991) Hippocampal activity in the presence of quinolones and fenbufen in-vitro (*Antimicrobial Agents and Chemotherapy*, 35, 1142-1146).

During the experiment the slices were held and treated in a special superfusion chamber (List Electronics, Darmstadt, Germany) according to (Haas, H L., Schaerer, B., Vosmansky, M. (1979). A simple perfusion chamber for the study of nervous tissue slices in vitro (*J Neurosci Methods*, 1, 323-5), at 35° C. (Schiff, S J., Somjen, G G. (1985) The Effects of Temperature on Synaptic Transmission in Hippocampal Tissue Slices (*Brain Research*, 345, 279-284)). The preparation was superfused with ACSF at 180-230 ml/h. Electric stimulation (200 µA constant current pulses of 200 µs pulse width) of the Schaffer Collaterals within the CA2 area and recording of extracellular field potentials from the pyramidal cell layer of CA1 (Dimpfel, W., Spüler, M., Dalhoff, A., Hoffmann, W., Schlüter, G. (1991) Hippocampal activity in the presence of quinolones and fenbufen in-vitro (*Antimicrobial Agents and Chemotherapy*, 35, 1142-1146).

Measurements were performed at 10 min intervals to avoid potentiation mechanisms. Four stimulations—each 20 seconds apart—were averaged for each time point. After obtaining three stable responses to single stimuli (SS) long-term potentiation was induced by applying a theta burst type pattern (TBS). The mean amplitude of three signals was averaged to give the mean of absolute voltage values (Millivolt)±standard error of the mean for four slices representing one of the experimental conditions.

Four slices were used from 1 rat per day taken one day after the daily administration by gavage of 5 mg/kg or 10 mg/kg Zembrin® or vehicle for one week. Additionally, slices from pre-treated rats (Zembrin® or control) were tested in the presence of different concentrations of glutamate receptor agonists listed in Table 1. The total alkaloid content of the batch of Zembrin® used in this example was 0.42% (by weight). The batch contained 11.91% mesembranol and 40.8% mesembrenol-(w/w) of the total alkaloids.

TABLE 1

Ingredients used during the experimental series.

| Test items | Charge | from |
|---|---|---|
| Zembrin ® | Ch.-B.: SCE0415-2105 | HG&H Pharmaceuticals Ltd. |
| Placebo (Control) 1% Glucose | Charge 38837487 | Carl Roth GmbH & Co. |

TABLE 1-continued

Ingredients used during the experimental series.

| Test items | Charge | from |
|---|---|---|
| (S)-(—)-5-Fluorowillardine | Batch no.: 9A/36714 | BIO TREND Chemikalien GmbH. |
| Trans-ACBD | Batch no.: 0048BN/01 | BIO TREND Chemikalien GmbH. |
| (±) trans-ACPD | Batch no.: 0053bn/01 | BIO TREND Chemikalien GmbH. |
| O-Phospho-L-Serin | Batch no.: 0400BN701 | BIO TREND Chemikalien GmbH. |

The Rats were treated daily for one week with 5 mg/kg or 10 mg/kg of Zembrin® or control. Changes of the excitability of the hippocampus were examined the next day by using in vitro slices. The results illustrated in FIG. 1 were obtained after performance of single stimuli (10-80 min) and after burst stimuli (90-120 min) on the hippocampus of a subject. Data is shown as mean±S.E.M. of n=12 slices from 3 animals/group.

Figure 1:
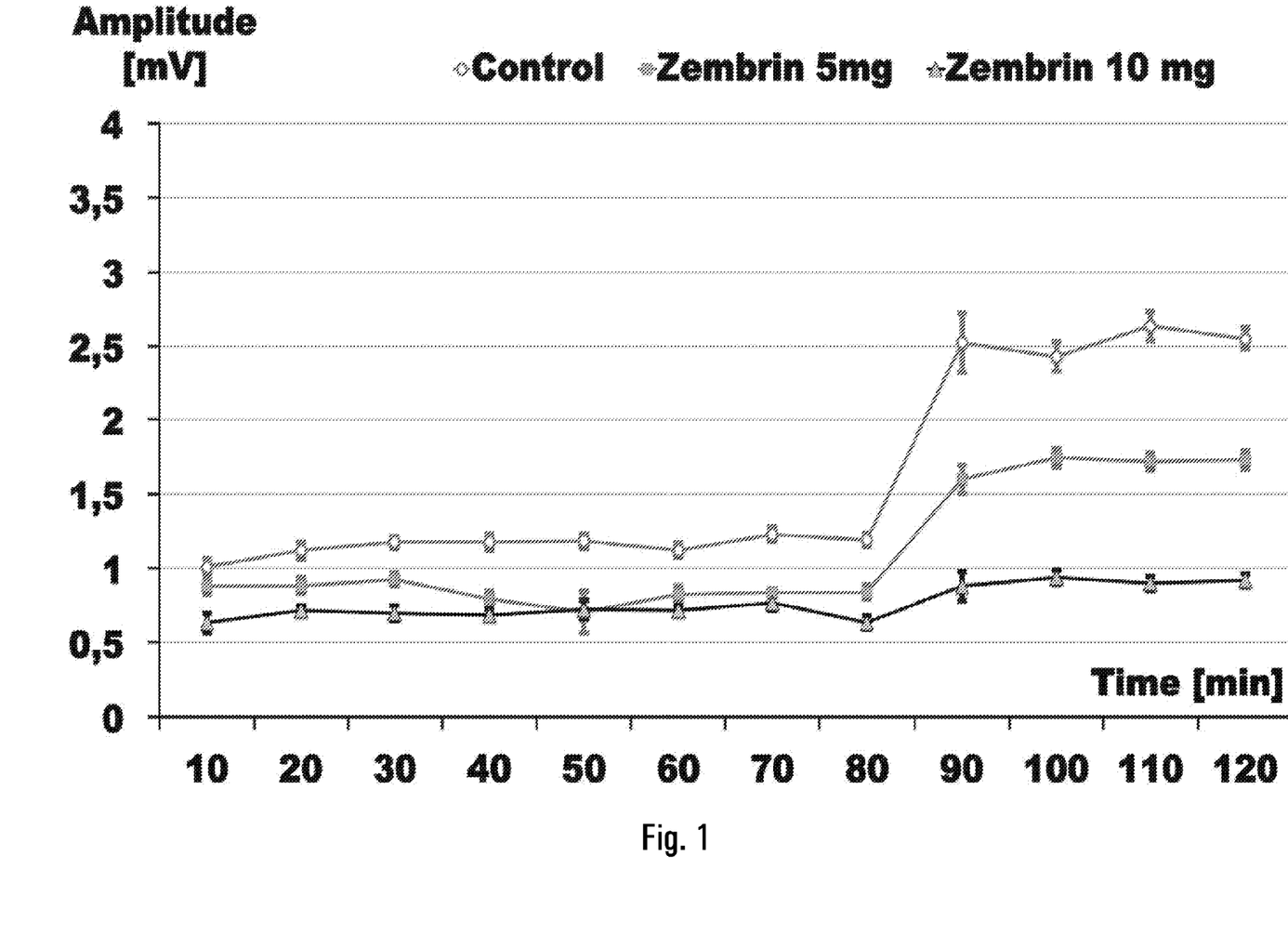
FIG. 1 Dose dependent effects of Zembrin® on pyramidal cell activity in terms of changes of population spike amplitudes (as voltage on the ordinate).

Electric stimulation of the Schaffer collaterals resulted in responses of the pyramidal cells recorded as a population spike. Amplitudes up to 4 mV were recorded under different experimental conditions representing the number of recruited pyramidal cells. FIG. 1 illustrates that slices from animals pre-treated for one week daily with 5 mg/kg of Zembrin® showed a lower excitability in as much as population spike amplitudes achieved after single stimuli, as well as after theta burst stimulation were significantly lower than under control conditions.

From FIG. 1 it can be also be seen that, based on ex vivo investigations on slices of the hippocampus, Zembrin® induces a suppression of the pyramidal cell activity both after single stimulation and a suppression of long-term potentiation.

Figure 2:
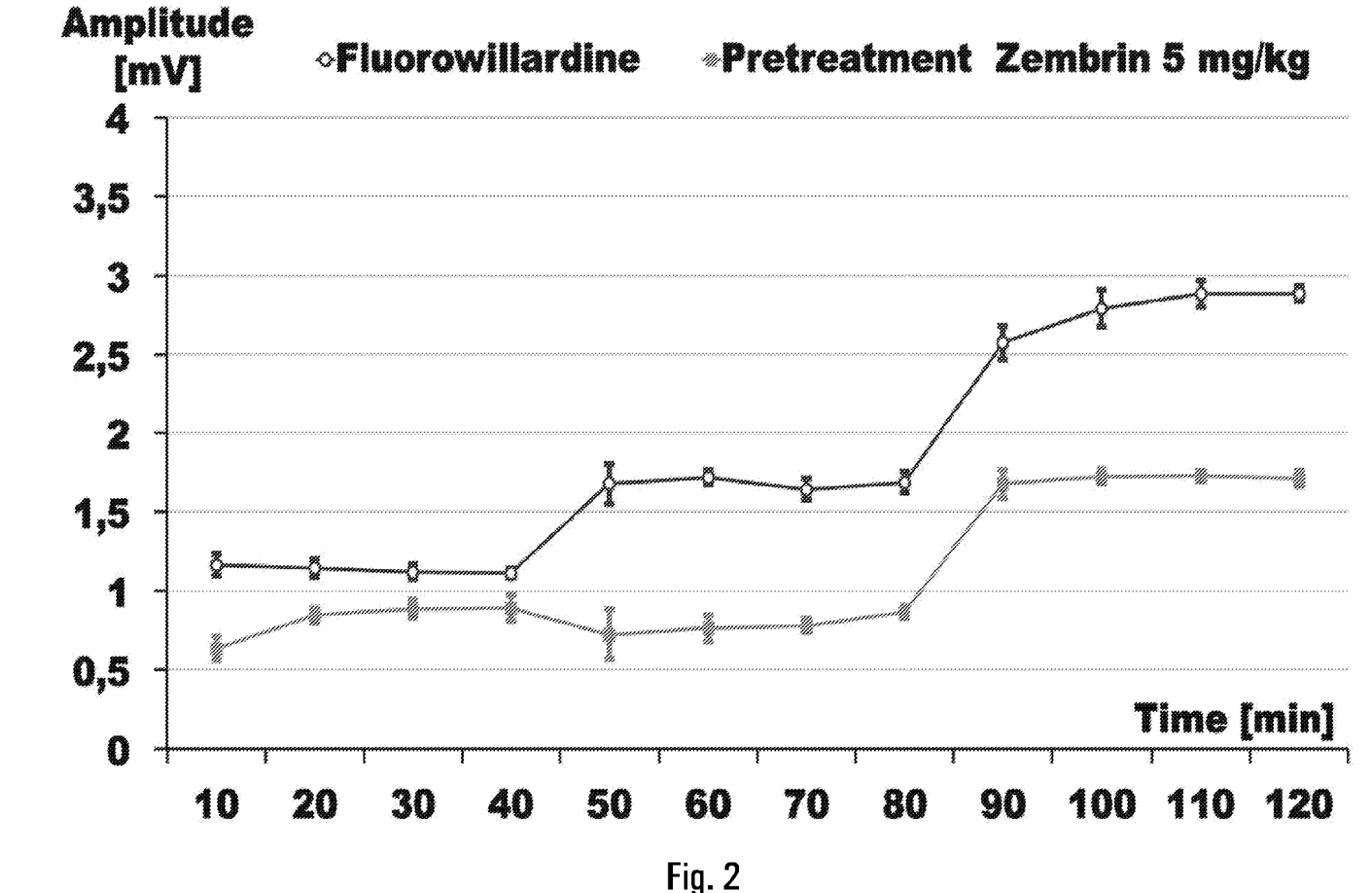
FIG. 2 Effect of (s)-(−)-5-Fluorowillardine in vitro and lack of its effect on pyramidal cell activity in slices of the hippocampus of rats pre-treated with 5 mg/kg of Zembrin®.

In order to test a possible interference of Zembrin® with AMPA receptor activated signal changes, the glutamatergic neurotransmission was tested in the presence of (S)-(-)-5-Fluorowillardine, a very potent and selective competitive AMPA receptor agonist. The results are illustrated in FIG. 2 of the drawings. In the presence of 0.10 μM (S)-(-)-5-Fluorowillardine responses matched completely those as obtained in slices from animals pretreated for one week with 5 mg/kg of Zembrin®. The AMPA receptor agonist was not able to exert its action in slices from Zembrin® pre-treated animals. The results illustrated in FIG. 2 are from single slices as obtained after single stimuli (60-80 min on abscissa) or after burst stimuli (TBS) (100-120 min). Data are given as mean±S.E.M. Amplitude of the signal is given as voltage in mV (ordinate). It can be seen that a strong interaction of Zembrin® with AMPA receptor mediated neuronal transmission can be deduced from the results.

Intra-hippocampal communication is modulated by different glutamate receptors, which either are related directly to ion channels (NMDA and AMPA) or act via metabotropic changes. Highly potent agonists at these receptors induce a significant increase of the population spike amplitudes in the presence of single shock stimuli and during theta burst stimulation.

Figure 3:
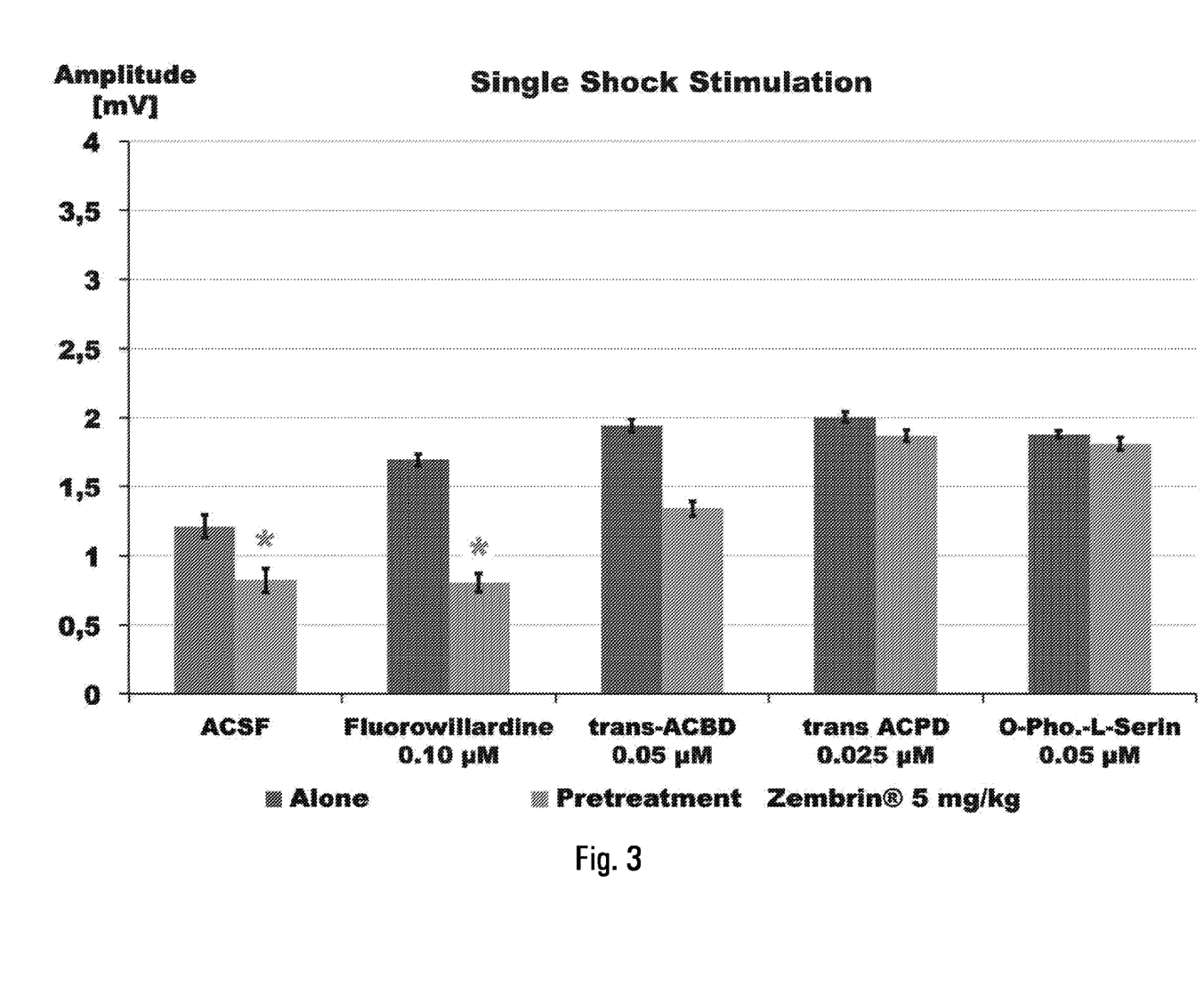
FIG. 3 Effects of single stimuli of 5 mg/kg of Zembrin® in presence of glutamate receptor agonists.

In FIG. 3, the dark shaded bar graphs represent the action of glutamate receptor agonists alone, which is based on reference data from an earlier experimental series. The grey (lighter) graphs show the population spike amplitudes measured in slices from animals pre-treated with 5 mg/kg Zembrin®. Statistical significance of p<0.01 is marked by stars. FIG. 3 provides an overview of data obtained by single shock stimulation. The results shown in FIG. 3 are from slices as obtained after single stimuli. Data are given as mean±S.E.M. Amplitude of the signal is given as voltage in mV (y-axis).

The results of FIG. 3 illustrate that fluorowillardine, specifically acting on the AMPA receptor was not able anymore to induce an increase of the population spike in Zembrin® pre-treated animals. Trans ACPD was only partially active in Zembrin® pre-treated animals. Thus, it can be concluded that Zembrin® interacted only with ionotropic receptor mediated electric activity.

Figure 4:
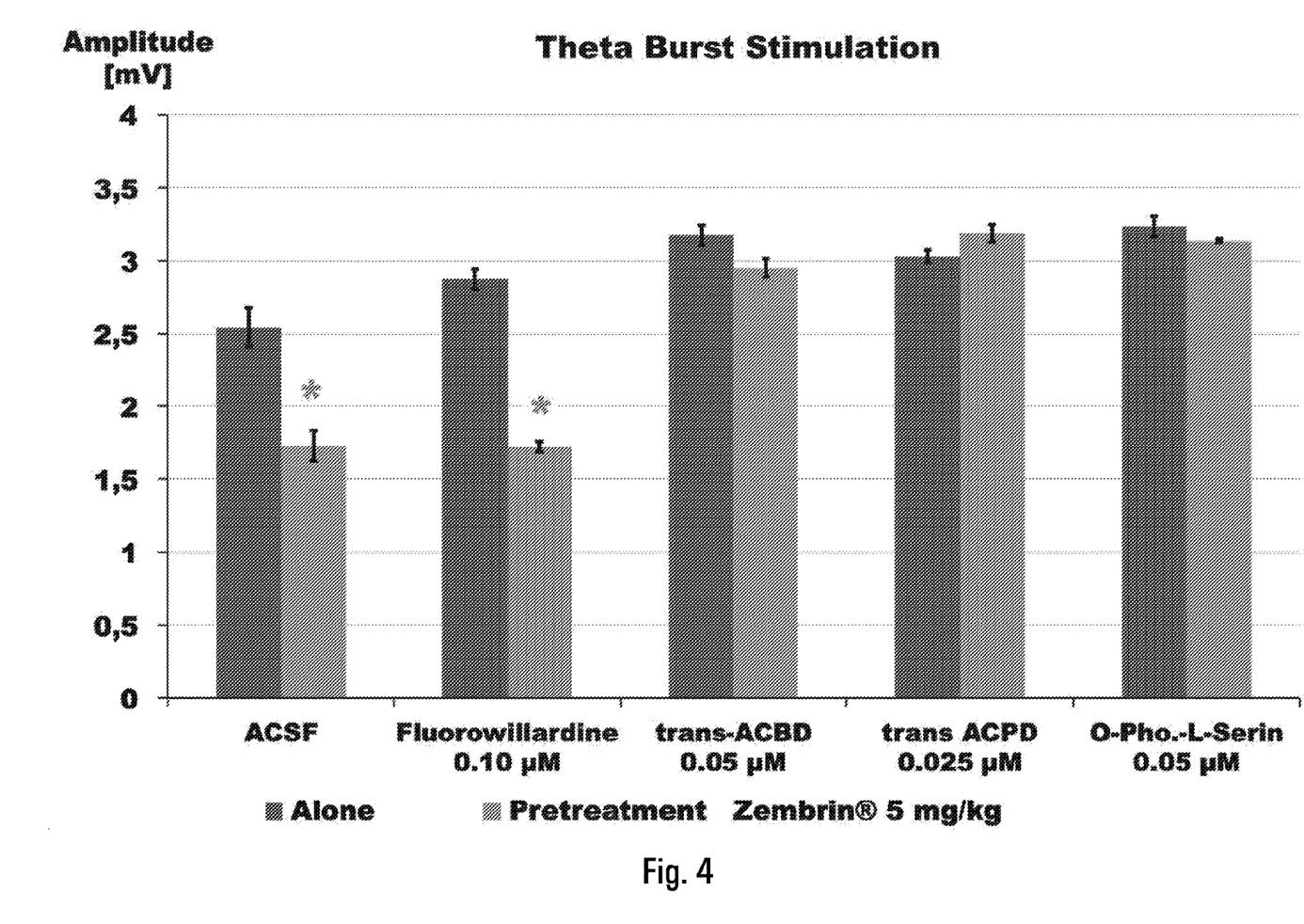
FIG. 4 Effects of theta burst stimulation of 5 mg/kg of Zembrin® in presence of glutamate receptor agonists.

FIG. 4 shows results from slices as obtained during theta burst stimulation. Data are given as mean±S.E.M. Amplitude of the signal is given as voltage in mV (y-axis). In FIG. 4, the dark bar graphs represent the action of glutamate receptor agonists alone (reference data from an earlier experimental series) and grey (lighter) graphs show the population spike amplitudes measured in slices from animals pre-treated with 5 mg/kg Zembrin®. The statistical significance of p<0.01 is marked by stars.

EXAMPLE B

Figure 5:
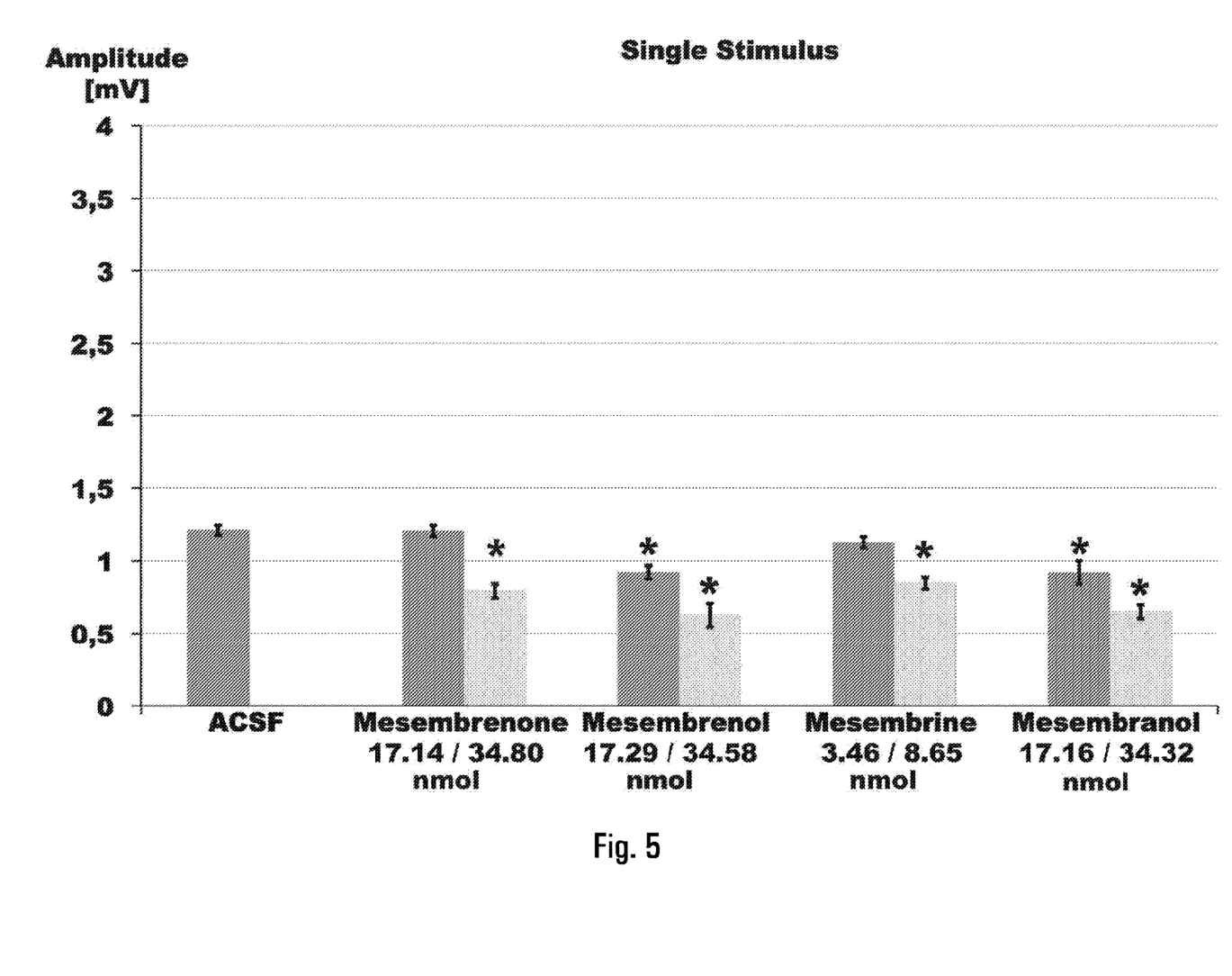
FIG. 5 Amplitude of population spike in the presence of artificial cerebrospinal fluid (ACSF) or two different concentrations of Zembrin® alkaloids during single shock stimulation.
Figure 6:
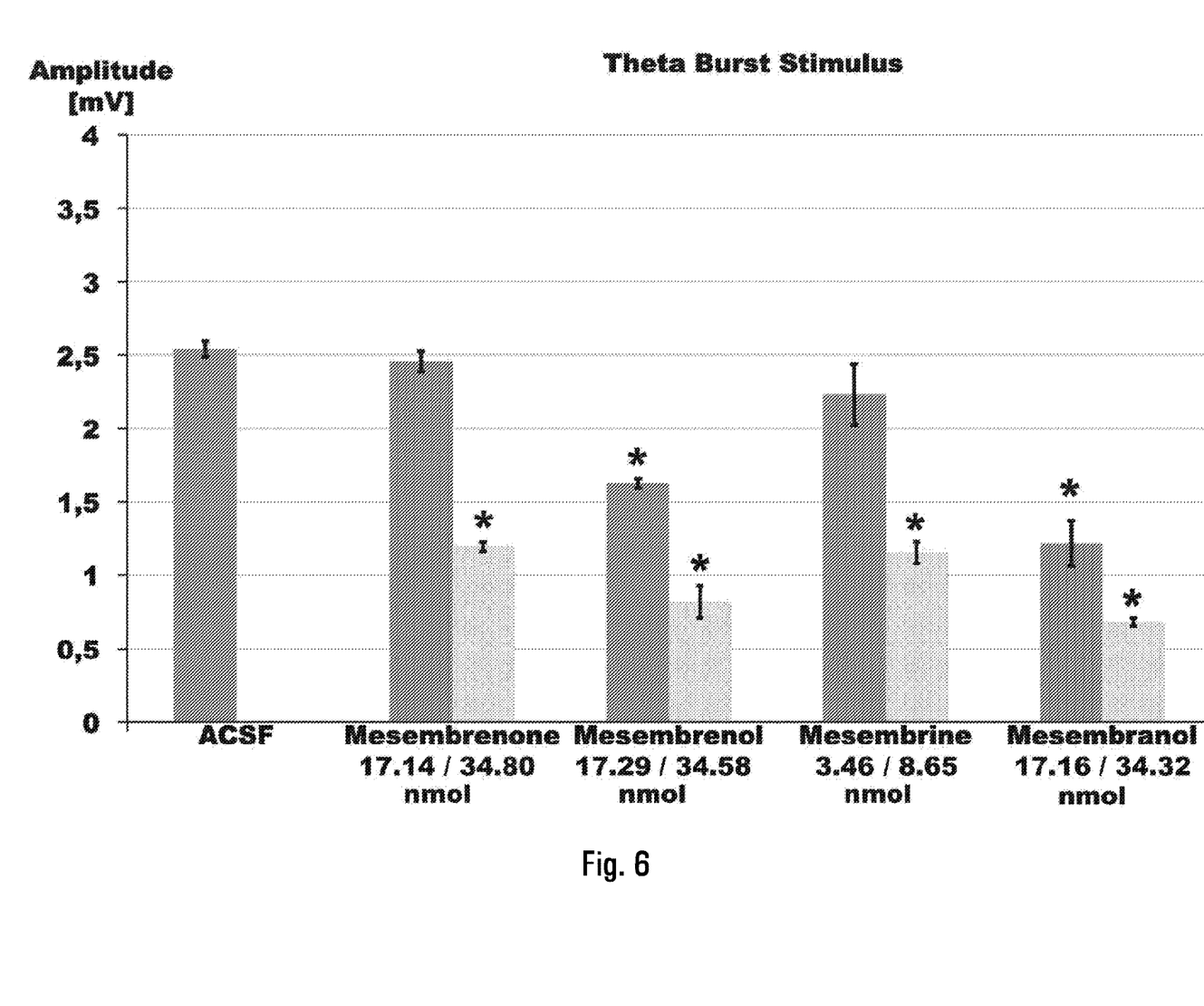
FIG. 6 Amplitude of population spike in the presence of artificial cerebrospinal fluid (ACSF) or two different concentrations of Zembrin® alkaloids during theta burst stimulation.
Figure 7:
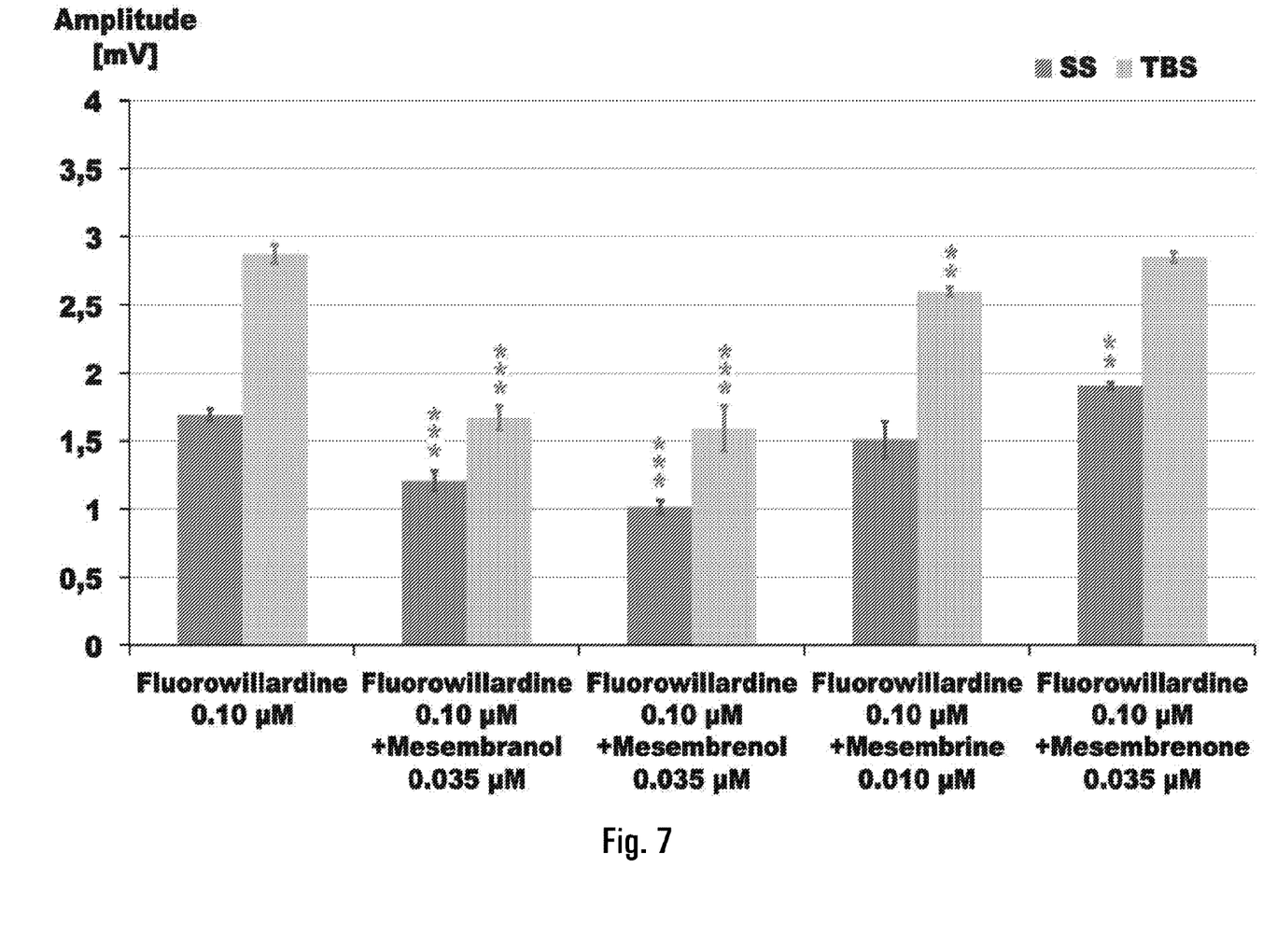
FIG. 7 Amplitude of population spike in the presence of Fluorowillardine alone or together with the four Zembrin® alkaloids.

Four important alkaloids contained in Zembrin® namely, mesembrenone, mesembrenol, mesembrine and mesembranol, were individually isolated. Similar tests to those described in example A were carried out on each of these isolated alkaloids, in the presence of two concentrations in the nanomolar range and the results are illustrated in FIGS. 5 to 7. Data obtained under the condition of single shock stimuli are presented in FIG. 5. In FIG. 5, the statistical significance of p<0.01 is marked by stars. Data obtained under the condition of theta burst stimuli are shown in FIG. 6. In FIG. 6, the statistical significance of p<0.01 is marked by stars. In FIG. 7, mean values of 3 slices are depicted for each recording condition. Statistical significance between Fluorowillardine alone and the presence of the alkaloids is documented by stars. (=p<0.05; *=p<0.01).

Of the four alkaloids only mesembranol and mesembrenol interact with AMPA mediated transmission, as can be seen in FIG. 7 of the illustrations.

However, FIGS. 5 and 6 of the illustrations reveal that all of them are able to attenuate the population spike amplitude to a significant degree. However, mesembrenol and mesembranol induced a stronger attenuation in comparison to mesembrine and mesembrenone.

It should be noted that mesembrine was tested at lower concentrations exerting a similar extent of attenuation at 8.65 nM as the other alkaloids at about 17 nM.

AMPA receptors are key mediators of pathological electrochemical events in focal epilepsies, including the paroxysmal depolarization shift (the basis of the EEG spike) and the electrographic seizure discharge. In addition to mediating synchronous discharges in epileptic foci, AMPA receptors are critically important in the spread of seizure activity locally and to distant brain regions. Since the early 1980s, it has been known that pharmacological inhibition of ionotropic glutamate receptors can protect against seizures in experimental models (Rogawski, M A. (2016) A fatty acid in the MCT ketogenic diet for epilepsy treatment blocks AMPA receptors (*Brain,* 139, 306-9)).

AMPA-antagonistic actions have been reported to be the mechanism of action of various antiepileptic drugs (Steinhoff, B. J. (2015). The AMPA receptor antagonist Perampanel in the adjunctive treatment of partial-onset seizures: clinical trial evidence and experience (*Ther Adv Neurol*

Disord, 8, 137-47). Likewise, Rohracher et al, 2016 mention the efficacy of the AMPA receptor antagonist Perampanel against primary generalized tonic-clonic seizures (Rohracher, A., Brigo, F., Höfler, J., Kallss, G., Neuray, C., Dobesberger, J., Kuchukhidze, G., Leitinger, M., Trinka, E. (2016)). Perampanel for the treatment of primary generalized tonic-clonic seizures in idiopathic generalized epilepsy (Expert Opin Pharmacother 17, 1403-11). Snoeijen-Schouwenaars et al., 2017 document the efficacy of the AMPA antagonist Perampanel in epileptic patients (Snoeijen-Schouwenaars F M, van Ool J S, Tan I Y, Schelhaas H J, Majoie M H (2017). Evaluation of perampanel in patients with intellectual disability and epilepsy (*Epilepsy Behav*, 66, 64-67).

Further evidence for antiepileptic activity from a different AMPA receptor antagonist in rodents and patients has been described by Orain et al., 2017 (Orain, D., Tasdelen, E., Haessig, S., Koller, M., Picard, A., Dubois, C., Lingenhoehl, K., Desravaud, S., Floersheim, P., Carache, D., Urwyler, S., Kallen, J., Mattes, H. (2017). Design and Synthesis of Seluramanel, a Novel Orally Active and Competitive AMPA Receptor Antagonist (*Chem Med Chem*, 12, 197-201).

AMPA receptor inhibition as mechanism of action for anti-seizure activity has been proven also for decanoic acid by Chang et al., 2016 (Chang, P., Augustin, K., Boddum, K., Williams, S., Sun, M., Terschak J A., Hardege, J D., Chen, P E., Walker, M C., Williams, R S B. (2016) Seizure control by decanoic acid through direct AMPA receptor inhibition (*Brain*, 139, 431-43).

Accordingly, the alkaloids mesembranol and mesembrenol, as well as Zembrin® which contains mesembranol and mesembrenol demonstrate AMPA receptor antagonist properties, arising out of which it would be readily apparent that these active ingredients independently, or in combination, have an anti-epileptic action and can be used in the treatment of patients suffering from epilepsy, a condition associated with epilepsy or seizures associated with epilepsy.

Compositions of which the applicant is aware which are commonly used for the treatment of epilepsy have a wide range of side effects, in particular with regard to the occurrence of changes in blood counts, as well as kidney and liver damage.

Accordingly, the alkaloids mesembranol and mesembrenol, as well as Zembrin® which contains mesembranol and mesembrenol demonstrate AMPA receptor antagonist properties, arising out of which it would be readily apparent that these active ingredients independently, or in combination, have an anti-epileptic action and can be used in the treatment of patients suffering from epilepsy, a condition associated with epilepsy or seizures associated with epilepsy Compositions of which the applicant is aware which are commonly used for the treatment of epilepsy have a wide range of side effects, in particular with regard to the occurrence of changes in blood counts, as well as kidney and liver damage. Almost all known compositions for treating epilepsy of which the applicant is aware are detrimental to a patient's capacity of reaction and therefore negatively affect a patient's fitness to drive. Currently, many forms of epilepsy cannot be effectively controlled with medicine. Often, a surgery, which has various associated risks, is the only treatment option for a patient suffering from epilepsy.

Thus, there exists a need for an improved composition with a good therapeutic effect and with the lowest possible side-effect rate. Typically, a composition with a low side-effect rate involves a natural product. Extracts from the family Mesembryanthemaceae containing the alkaloids mesembrenol and mesembranol have been shown to have very high maximum tolerated doses and no-observed-adverse-events levels (Murbach et al (2014) *A toxicological safety assessment of a standardized extract of Sceletium tortuosum (Zembrin) in rats Food and Chemical Toxicology* 74:190-199), and good tolerability and low reported side effects when used as a daily supplement in humans (Nell et al (2013) *A Randomized, Double-Blind, Parallel-Group, Placebo-Controlled Trial of Extract Sceletium tortuosum (Zembrin) in Healthy Adults. J Alt Compl Medicine* 18:1-7). This would make a natural product derived from the plant or extract an attractive composition for the delivery of the alkaloids.

The invention claimed is:

1. A method of treating a disease that responds to treatment with an α-amino-3-hydroxy-5-methyl-4-isoxazolepropionic acid (AMPA) receptor antagonist, comprising administering to an individual in need thereof a composition comprising a total alkaloid content of between 0.35% and 0.45% (by weight), with mesembranol comprising at least 5% (w/w) of the total alkaloid content, and mesembrenol comprising over 40% (w/w) of the total alkaloid content, in an amount effective to attenuate AMPA mediated neurotransmission in hippocampus of the individual, wherein attenuation of AMPA mediated neurotransmission in the hippocampus of the individual is effected by inducing a suppression of pyramidal cell activity upon administration of the composition.

2. The method of claim 1, wherein the disease that responds to treatment with the AMPA receptor antagonist is epilepsy or a condition associated with epilepsy.

3. The method of claim 2, wherein the condition associated with epilepsy is migraine, a cerebrovascular and cardiovascular disorder, a gastrointestinal disorder, a pulmonary disorder, dementia, chronic fatigue, depression, a mood disorder, anxiety, a personality disorder, a psychotic disorder, a non-epileptic seizure, cognitive dysfunction, an antiepileptic drug (AED)-related neurobehavioral disorder, suicidality, or a behavioral/psychiatric disturbance.

4. The method of claim 1, wherein the composition comprises an extract of *Sceletium tortuosum*.

5. The method of claim 1, wherein the individual is suffering from the disease that responds to treatment with the AMPA receptor antagonist.

6. A method of modulating an α-amino-3-hydroxy-5-methyl-4-isoxazolepropionic acid (AMPA) receptor activity in an individual in need thereof, comprising administering to the individual a composition comprising a total alkaloid content of between 0.35% and 0.45% (by weight), with mesembranol comprising at least 5% (w/w) of the total alkaloid content, and mesembrenol comprising over 40% (w/w) of the total alkaloid content, in an amount effective to attenuate AMPA mediated neurotransmission in hippocampus of the individual, wherein attenuation of AMPA mediated neurotransmission in the hippocampus of the individual is effected by inducing a suppression of pyramidal cell activity upon administration of the composition.

7. The method of claim 6, wherein the composition comprises an extract of *Sceletium tortuosum*.

8. The method of claim 6, wherein the individual is suffering from a disease that responds to treatment with an AMPA receptor antagonist.

9. The method of claim 8, wherein the disease that responds to treatment with the AMPA receptor antagonist is epilepsy or a condition associated with epilepsy.

10. The method of claim 7, wherein the disease that responds to treatment with the AMPA receptor antagonist is epilepsy or a condition associated with epilepsy.

11. The method of claim 9, wherein the condition associated with epilepsy is migraine, a cerebrovascular and cardiovascular disorder, a gastrointestinal disorder, a pulmonary disorder, dementia, chronic fatigue, depression, a mood disorder, anxiety, a personality disorder, a psychotic disorder, a non-epileptic seizure, cognitive dysfunction, an antiepileptic drug (AED)-related neurobehavioral disorder, suicidality, or a behavioral/psychiatric disturbance.

\* \* \* \* \*